US00PP10166P

United States Patent [19]

Nicholson

[11] Patent Number: Plant 10,166

[45] Date of Patent: Dec. 30, 1997

[54] DOGWOOD TREE 'COMCO NO. 1'

[75] Inventor: Hubert A. Nicholson, deceased, late of Decherd, Tenn., by Mary J. Nicholson, executor

[73] Assignee: Commercial Nursery Co., Inc., Decherd, Tenn.

[21] Appl. No.: 463,024

[22] Filed: Dec. 18, 1995

[51] Int. Cl.[6] ..... A01H 5/00

[52] U.S. Cl. ..... Plt./53.2

[58] Field of Search ..... Plt./53.2

[56] References Cited

U.S. PATENT DOCUMENTS

| | | | |
|---|---|---|---|
| P.P. 1,710 | 5/1958 | Hawkersmith | Plt./53.2 |
| P.P. 3,993 | 12/1976 | Steppe | Plt./53.2 |
| P.P. 8,214 | 4/1993 | Orton et al. | Plt./53.2 |

*Primary Examiner*—James R. Feyrer
*Attorney, Agent, or Firm*—Frank B. Robb; John H. Vynalek

[57] ABSTRACT

A distinctive Dogwood cultivar of the *Cornus florida* genus and species having bracts which present an overall strong red appearance with white portions at the base of the bracts and white apical notches, the plant being vigorous and with distinct purplish red new growth, and resistance to powdery mildew.

2 Drawing Sheets

This application is a substitute for application Ser. No. 08/201,380, filed Feb. 24., 1994, abandoned in the Patent Office.

BACKGROUND OF THE INVENTION

This invention relates to dogwood trees and more specifically to one of the *Cornus florida* genus and species.

In a large nursery with which I am associated, near Decherd, Tenn., we grow large quantities of Dogwood and as would be expected under these circumstances, we often observe sports and chance seedlings which are attractive for one reason or another.

Such a circumstance is related to the instant plant, which I observed as a chance seedling growing among the large quantity of plants, and was particularly noticeable for a number of distinctive characteristics including distinct, purplish, new growth. The plant of this disclosure has been asexually reproduced by budding in the vicinity of Decherd, Tenn. While this tree has been named 'Comco No. 1' for purposes of international registration, it is anticipated that this tree will also be marketed in the United States under the synonym "Cherokee Brave".

SUMMARY OF THE INVENTION

The striking features of the instant plant includes its extreme vigor, being twice the size of seedlings of other *C. florida* varieties, and also the striking coloration of the foliage having a very rich burgundy red on the juvenile leaves with older leaves having a dark rich green color. Other distinctive characteristics include the size of the mature leaves which are much larger than leaves of other *C. florida* being typically one and one half times as large. In addition, the tree grows one and one half times faster than other red or pink flowering cultivars such as 'Cherokee Chief' and 'Rubra' The trunk remains smooth through maturity, as opposed to other cultivars, and the branch internode length is much larger than other cultivars. The plant is powdery mildew and disease resistant as opposed to other cultivars.

BRIEF DESCRIPTION OF THE DRAWING

This new variety of *Cornus florida* is illustrated by the accompanying photographic drawings which depict the plant by the best possible color representation using color photography. The first drawing herewith discloses a close-up of the bracts while the second drawing shows the full height of the plant both of which show the plant in as nearly true color as photography will provide.

It should be noted where color notations are used, reference is had to the charts of British Royal Horticultural Society, except where references to colors having ordinary dictionary significance seem to be appropriated.

DETAILED DESCRIPTION OF THE INVENTION

*Cornus florida* (Selected Seedling)

Tree: Rounded, upright branching habit and very spreading. Extreme vigor.

Trunk: Very smooth as a juvenile tree. Trees attaining a size of two and one-half caliper at base of the trunk still maintain a very smooth bark. Small one year liners after budding have shown good caliper which denotes good carbohydrate built up and produces the trees extreme vigor.

Branches: Very stocky, internodes are farther apart than other *C. florida* species. Very strong leader and upright appearance spreading with age. Fewer side branches give the an open appearance.

Leaves: Ovate shape, juvenile coloration red (51B) with mature coloration on upper surface is dark green (132A) with lower surface a lighter green, appear opposite one another, simple deciduous with entire margins, length: 4 ½–6 ½ inches, width: 2–3½ inches. The size of leaves gives the tree a full appearance with a dense canopy.

Petioles: ¼ to ½ inches long.

Floral bracts: Size: average 3½–4¼ inches in diameter. Color: Fully opened, deep red 51A overall fading to white at the central area where the bracts are connected at the base and the fruit clusters are present. The white portion is 1⅜–1½ inches in size. The base of each bract is white, close to the connection, each bract becoming the deep red to provide the overall red appearance. Apical notches which are white and ⅛ inch to ⅜ inch deep provide a prominent contrast to the overall red color which predominates. The flowering period is similar to that of other *C. florida* species. True flowers are small, yellowish.

Fruit: Typical fruit clusters wherein individual drupes are oval. Size: ⅜–½ inch long, and usually in clusters of six. Color: vivid red (51A).

Disease resistance: Resistant to powdery mildew and Anthracnose discula strain as shown by testing.

Drought resistance: Good drought resistance as opposed to other *C. florida species.*

Growth habit: The plant has a quite vigorous growth habit and performs better in full sun than when grown closer to fence rows or overhanging trees thus giving shade which results in the plant being smaller overall with a small leaf not showing in full color.

I claim:

1. A new and distinct variety of dogwood plant characterized particularly as to novelty by the flowering bracts of overall strong red color with white central areas and white apical notches, distinct purplish red new growth, and resitance to powdery mildew in open field conditions as compared with other cultivars.

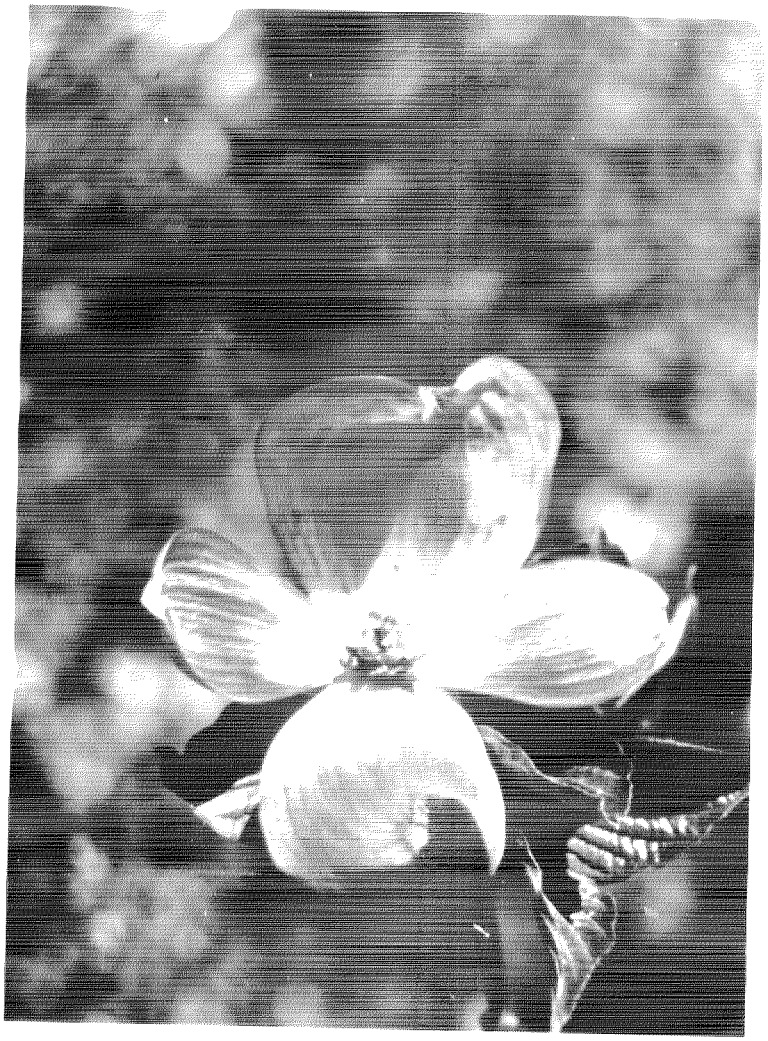

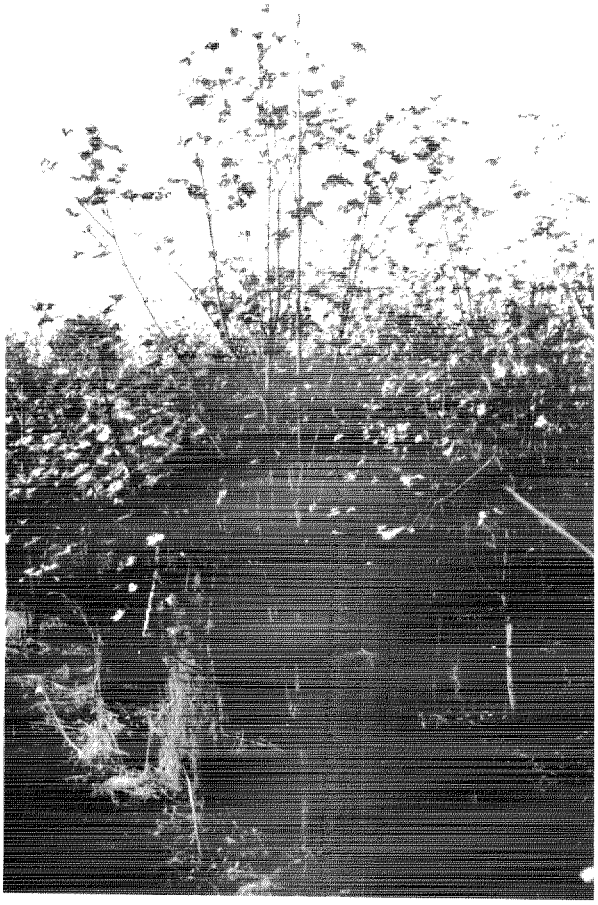

* * * * *